United States Patent [19]

Iten

[11] Patent Number: 5,016,353
[45] Date of Patent: May 21, 1991

[54] SUTURE CUTTER

[75] Inventor: Clemens A. Iten, Staunton, Va.

[73] Assignee: American Safety Razor Company, Verona, Va.

[21] Appl. No.: 830,873

[22] Filed: Feb. 19, 1986

[51] Int. Cl.$^5$ ............................................. B25F 3/00
[52] U.S. Cl. .................................................... 30/124
[58] Field of Search .................. 30/124, 134, 179; 128/305, 318

[56] References Cited

U.S. PATENT DOCUMENTS

| | | | |
|---|---|---|---|
| 3,054,182 | 9/1962 | Whitton, Jr. | |
| 3,266,493 | 8/1966 | Cummings | |
| 3,541,684 | 11/1970 | Beaver | |
| 3,576,072 | 4/1971 | Foster | 30/124 |
| 3,624,683 | 11/1971 | Matles | |
| 3,659,343 | 5/1972 | Straus | 30/124 |
| 3,879,846 | 4/1975 | Allen | |
| 3,972,333 | 8/1976 | Leveen | |
| 3,990,144 | 11/1976 | Schwartz | |
| 4,034,473 | 7/1977 | May | |
| 4,053,979 | 10/1977 | Tuthill et al. | 30/124 |
| 4,092,776 | 6/1978 | Ferguson | |
| 4,098,157 | 7/1978 | Doyle | 128/305 |
| 4,246,698 | 1/1981 | Lasner et al. | |

OTHER PUBLICATIONS

Silloway et al., "Innovations in Skin Suture Removal", The American Journal of Surgery, vol. 149, pp. 799-801, Jun. 1985.

Primary Examiner—Frank T. Yost
Assistant Examiner—Willmon Fridie
Attorney, Agent, or Firm—Nixon & Vanderhye

[57] ABSTRACT

A suture cutter of the chopper type uniquely adapted to permit using the blade portion as a probe to be inserted between the skin and a suture, with an opposed anvil portion not necessarily adapted to be used as a probe being brought in contact with the suture, thus capturing and severing it the suture between blade and anvil. Using the blade instead of the anvil as the probe permits design of an anvil which optimally serves its desired function.

12 Claims, 4 Drawing Sheets

SUTURE CUTTER

BACKGROUND OF THE INVENTION

The present invention relates to the field of surgical cutting instruments, and more specifically, to an instrument useful in cutting percutaneous sutures.

As with other surgical procedures, the task of suture removal has lead to a variety of instruments intended to make it both simpler and safer These instruments may generally be grouped into three categories. The first category consists of instruments having a single, unopposed knife blade. One using such an instrument inserts the blade between the skin and the suture, with the cutting edge of the blade engaging the suture. Then, a quick thrust away from the skin severs the suture material. The disadvantage of such instruments is that the pulling force transmitted by the suture from the knife to the skin, although slight, results in trauma to the surrounding tissue.

A second class of suture removal instruments utilizes scissors, i.e., a pair of blades which slide past each other, with the suture material being severed by the passing blades. These instruments do not transmit any significant tugging force to the skin, and thereby avoid any resultant trauma. On the other hand, they are manifestly more complex than a simple knife, and must be manufactured and maintained with a relatively high degree of precision in order to operate satisfactorily. Instruments of this type are disclosed in U.S. Pat. No. 4,246,698 to Lasner et al. and U.S. Pat. No. 3,541,684 to Beaver.

A third class of suture removal instrument has resulted from a desire to obtain the nontraumatizing advantages of scissors in an uncomplicated instrument not requiring a great deal of precision. These instruments seek to achieve this effect by opposing a single blade with a cutting block or anvil. These instruments might properly be called "choppers." Such instruments are shown, for example, in U.S. Pat. No. 3,659,343 to Straus. In such instruments, the anvil serves also as a probe to be inserted between the suture and skin. The cutting edge of the blade, disposed on another arm of the instrument, is then brought toward the anvil, thus capturing the suture between the cutting blade and the anvil and severing it. While such instruments are, in general, satisfactory for suture removal, they have been limited by the fact that the anvil also serves as a probe, which imposes design constraints compromising its operation as either. In other words, it has been necessary to dimension and configure the anvil/probe structure in a fashion which compromises both functions. It is therefore desirable to overcome this disadvantage by designing a suture cutter in which this compromise can be avoided.

SUMMARY OF THE INVENTION

The present invention resides in a suture cutter of the chopper type in which the blade functions as the probe, thus removing constraints on the design of the anvil and permitting provision of an anvil optimally suited to function as such. Specifically, the present invention resides in providing a suture cutter for cutting a suture in a skin surface, comprising a handle assembly including a first arm and a second arm substantially longitudinally coextensive with and coupled at one end to the first arm. The second arm thus has a free end resiliently spaced away from an opposed free end of the first arm. Cutting means are attached to the free end of the first arm for insertion between the suture and skin surface, the cutting means including a blade having a suture-side cutting edge and a skin-surface-side noncutting edge meeting at a leading point. The blade is attached to the first arm with the noncutting edge at a nonzero angle with respect to the length of the first arm so that the first arm assumes the nonzero angle with respect to the skin surface when the noncutting edge is parallel to the skin surface. An anvil is disposed on the free end of the second arm and movable into cooperative engagement with the cutting edge of the blade when the first and second arms are adducted.

BRIEF DESCRIPTION OF THE DRAWINGS

These and other aspects of the invention will be most readily understood from, the following written description read in conjunction with the drawings, in which.

DETAILED DESCRIPTION OF THE PREFERRED EMBODIMENTS

Figure 1:
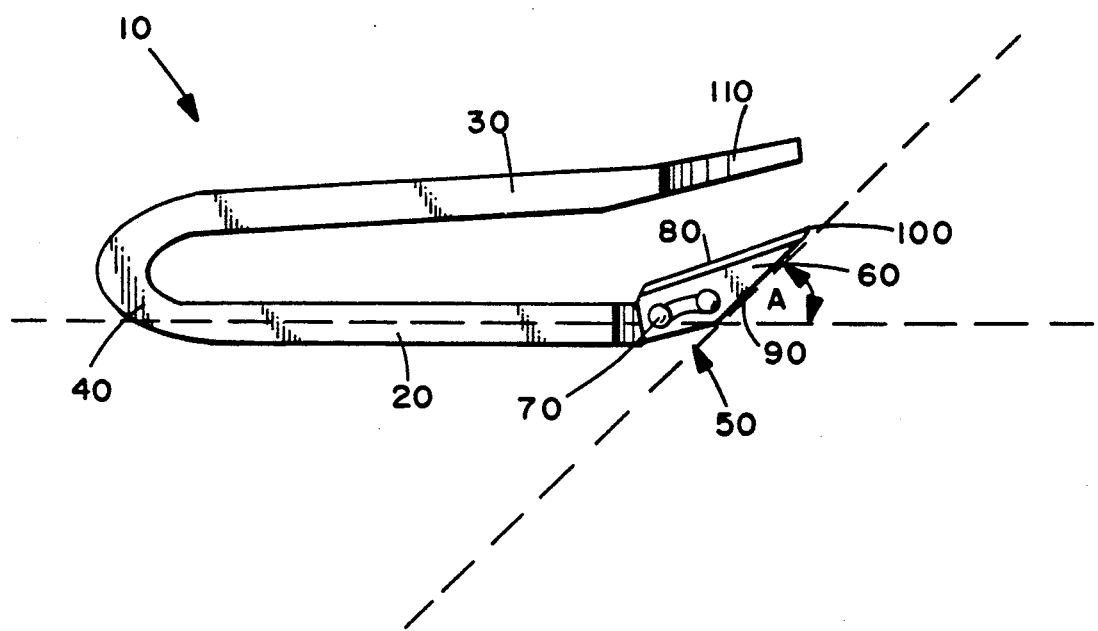
FIG. 1 is a side view of a first preferred embodiment of a suture cutter according to the present invention.

FIG. 1 shows a suture cutter according to the present invention, designated generally by numeral 10. This suture cutter has a first arm 20 and a second arm 30. These arms are coupled together at one end. In the embodiment of FIG. 1, the coupling is by a resilient neck portion 40. Also, in the embodiment of FIG. 1, the first arm 20, second arm 30, and neck portion 40 are integral, and preferably fashioned out of a resilient plastic.

Disposed at a free end of first arm 20 are cutting means designated generally by numeral 50. These cutting means include a blade 60 and blade retaining means 70. The blade retaining means 70 in the embodiment of FIG. 1 include two posts, mounted on an extension of first arm 20. The posts and extension of first arm 20 in the embodiment of FIG. 1 are integral with first arm 20.

Blade 60 includes a blade cutting edge 80 and a noncutting edge 90. Reflective of the orientation of these edges when the suture cutter is in use, edge 80 is referred to herein as the suture-side cutting edge, and edge 90 as the skin-surface-side noncutting edge. Skin-surface-side noncutting edge 90 and blade 60 generally are oriented so that skin-surface-side noncutting edge 90 forms an angle A with a line passing longitudinally through the major portion of arm first 20. The suture-side cutting edge 80 and the skin-surface-side noncutting edge 90 meet at a leading point 100.

Disposed on the free end of second arm 30 is anvil 110. In the embodiment shown in FIG. 1, anvil 110 is an integral extension of second arm 30. Anvil 110 is preferably made of plastic or other material which will not dull cutting edge 80 when cutting edge 80 is brought into contact with anvil 110. If arm 30 is made out of a material which would dull cutting edge 80, then a sleeve or coating of an appropriate material may be placed on anvil 110.

Suture-side cutting edge 80 and the opposed interior face of anvil 110 are arranged one with respect to the other so that leading point 100 contacts the anvil before the rest of suture-side cutting edge 80. The application of additional pressure thereafter continuously brings the rest of suture-side cutting edge 80 into engagement with anvil 110 in a front-to-back cutting action. This creates a front-to-back cutting action which is the opposite of the back-to-front cutting action characteristic of scissors.

Figure 2:
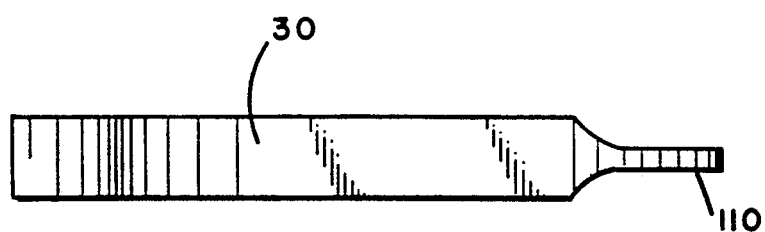
FIG. 2 is a top view of the suture cutter shown in FIG. 1.

FIG. 2 shows the configuration of the anvil 110 in greater detail. As mentioned above, greater latitude is permitted in configuring and dimensioning the anvil 110 because the anvil 110 need not be shaped or sized to be used as a probe to be inserted between the skin surface and the suture. Thus, it is easier to fashion anvil 110 so that has sufficient rigidity to oppose the blade 60 effectively. At the same time, it is still desirable that anvil 110 not be so large as to block the vision of the operator during suture cutting. Toward this end, in the embodiment of FIGS. 1 and 2, anvil 110 is thinner and narrower than the major portion of second arm 30. It is also possible to fabricate arm 30 and anvil 110 out of a transparent material to provide the operator even greater visibility.

Figure 3:
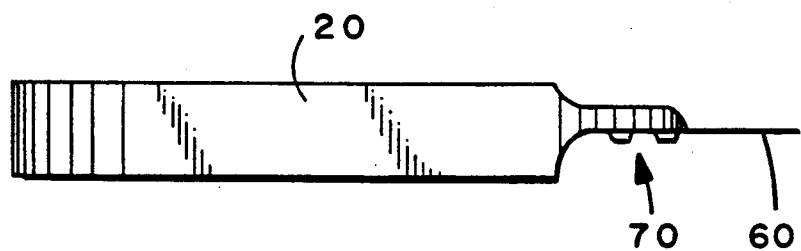
FIG. 3 is a top view of the suture cutter shown in FIG. 1 with the upper arm removed.

FIG. 3 is the same view as FIG. 2, with the second arm 30 removed to give a better view of first arm 20. As can be seen, blade 60 may be easily attached to first arm 20 through blade retaining means 70, which, in the embodiment of FIG. 3, is an integral offset projection of first arm 20, with two posts for securing blade 60. The projection is offset so that the blade can be centered. It will also be noted that in the embodiment of FIG. 3, at least one surface of the blade is almost completely unobstructed, which also facilitates the operator's ability to see what he or she is doing.

Figure 4:
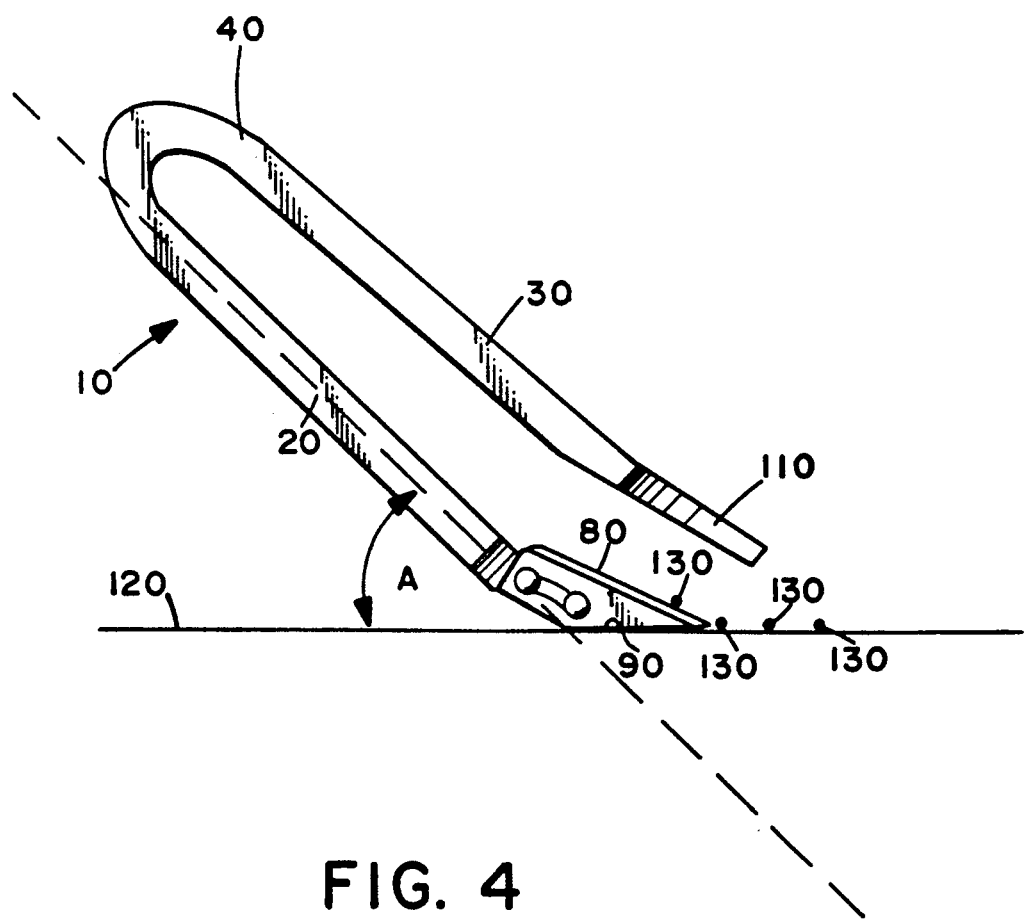
FIG. 4 is a diagram illustrating how the suture cutter shown in FIG. 1 would be used.

FIG. 4 has been provided to aid in explanation of how a suture cutter according to FIGS. 1, 2, and 3 would be used. In FIG. 4, the skin surface is represented by line 120. Numeral 130 designates sutures which have been placed in the skin. The suture cutter 10 is oriented so that skin-surface side noncutting edge 90 is parallel to skin-surface 120. Thus, the first arm 20 forms angle A with skin surface 120. As can be seen, leading point 100 of blade 60 is inserted between the suture 130 and skin surface 120. Anvil 110 is then brought down on the suture, and the suture material is severed. It can be appreciated that the operation is very simple, very easy, and effected with minimal trauma to the skin in which the suture has been placed.

Figure 5A:
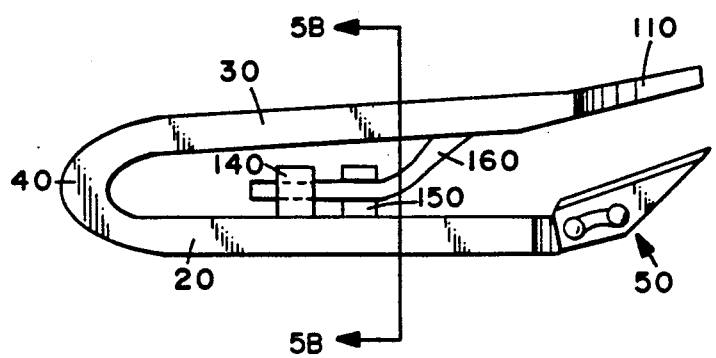
FIG. 5A is a side view of a second preferred embodiment of a suture cutter according to the present invention.
Figure 5B:
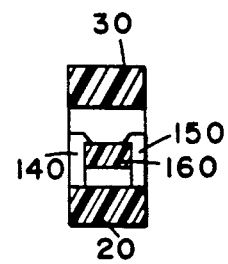
FIG. 5B is a cutaway view taken along line X—X of FIG. 5A.
Figure 5C:
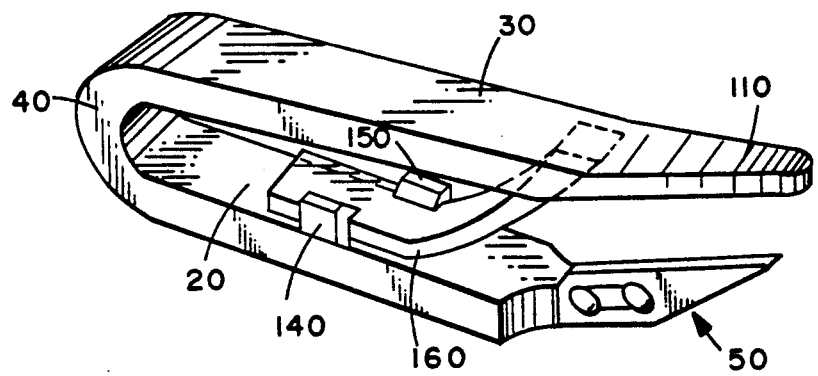
FIG. 5C is a perspective view of the suture cutter of FIGS. 5A and 5B.

In general, proper dimensioning and selection of materials provides sufficient lateral rigidity of the arms that additional measures for assuring such are not necessary. In applications where additional lateral rigidity is necessary or desirable, however, a lateral stabilizer such as that shown in FIGS. 5A, 5B and 5C may be used. The suture cutter of these figures is substantially the same as that just described, except for the addition of a lateral stabilizer including a first and second projections 140 and 150 on first arm 20, and a tongue 160 disposed on second arm 30. First and second projections 140 and 150 have inwardly-projecting upper ridges which retain tongue 160 between the projections. It will be readily appreciated that first and second projections 140 and 150 define the maximum lateral motion of tongue 160, and so the maximum lateral motion of second arm 30 with respect to first arm 20.

Figure 6:
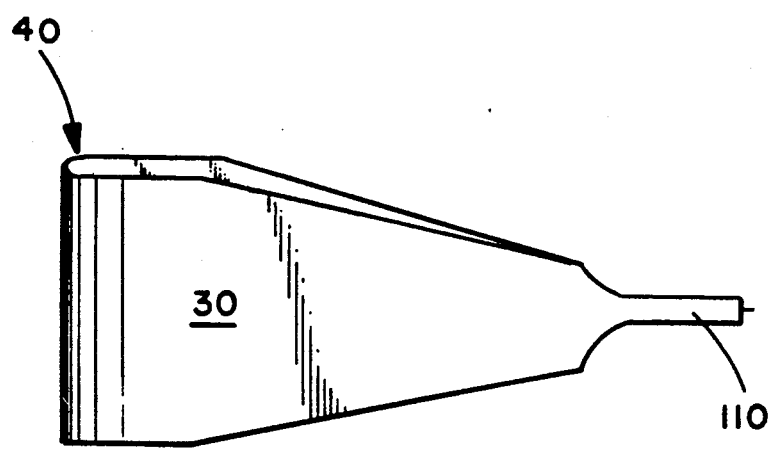
FIG. 6 is a top view of a third preferred embodiment of a suture cutter according to the present invention.

FIG. 6 shows another arrangement which may be used to provide greater lateral stability. In FIG. 6, first arm 20 (not visible) and second arm 30 do not have the elongated, rectangular configuration as they have in the embodiments of FIGS. 1-5. Instead, the configuration of second arm 30 is substantially triangular, with the apex of the triangle supporting the anvil 110, and the base of the triangle joining a neck portion 40 which is substantially wider than the neck portion 40 in the embodiments of FIGS. 1-5. First arm 20 has a configuration substantially the same as that of second arm 30, and is substantially coextensive therewith. The broadening of neck portion 40 results in greater lateral rigidity, thus minimizing relative lateral motion of first arm 20 and second arm 30.

Figure 7:
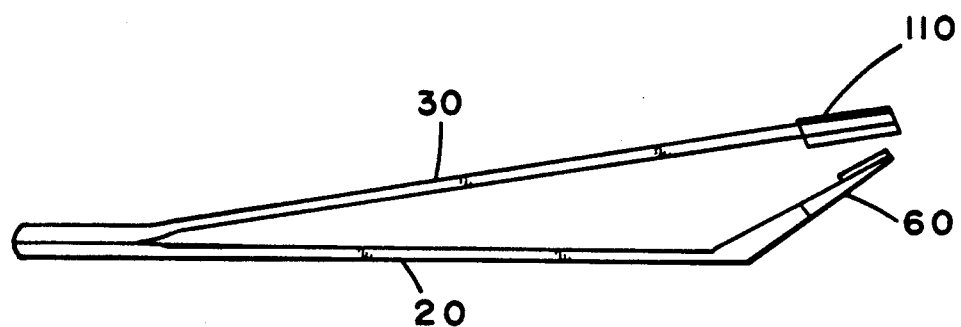
FIG. 7 is a side view of a fourth preferred embodiment of a suture, cutter according to the present invention.

In the embodiments just described, the first and second arms 20 and 30 and neck portion 40 are preferably integral with one another, and preferably formed of plastic material. The embodiment of FIG. 7, on the other hand, has no neck portion 40. Instead, first and second arms 20 and 30 are formed of a metallic material, and joined directly together at one end. The free end of first arm 20 has cutting means 50 in the form of a blade 60 similar to that in the previous embodiments. Second arm 30 has an anvil 110 which, instead of being simply an integral extension of second arm 30, comprises an extension of arm 30 with a sleeve 190 of nondulling material covering at least that portion of anvil 110 which comes in contact with the cutting edge of blade 60.

The foregoing description of four specific embodiments of the present invention has been provided for the purposes of illustrating the principles of the invention only. It will be apparent to one of ordinary skill in the art that these embodiments by no means exhaust all possible configurations, adaptations, and modifications of the present invention. To the contrary, one of ordinary skill in the art will readily appreciate that many modifications can be made to the embodiments discussed above without departing from the fundamental principles of the invention. The invention should therefore not be regarded as limited to any of the specific embodiments described above, but instead should be regarded as being fully commensurate in scope with the following claims.

What is claimed is:

1. A suture cutter for cutting a suture in a skin surface, comprising:
   a handle assembly including a first arm and a second arm substantially longitudinally coextensive with and coupled at one end to said first arm, said second arm having a free end spaced away from an opposed free end of said first arm;
   cutting means attached to said free end of said first arm for insertion between said suture and said skin surface, said cutting means comprising a blade having a straight suture-side cutting edge and a skin-surface-side noncutting edge meeting at a leading point, with said noncutting edge oriented at a nonzero angle with respect to the length of said first are so that said first arm assumes said nonzero angle with respect to said skin surface when said noncutting edge is parallel to said skin surface; and an anvil disposed on said free end of said second are and movable into cooperative engagement with said cutting edge of said blade as said first and second arms are adducted, said suture-side cutting edge engaging said anvil front-to-back when said first and second arms are adducted, with said leading point engaging said anvil first.

2. A suture cutter as claimed in claim 1 wherein said point of said blade is substantially laterally unobstructed to facilitate insertion between said skin surface and said suture.

3. A suture cutter as claimed in claim 1 wherein said handle assembly further includes a U-shaped neck portion connecting and integrally formed with said first and second arms.

4. A suture cutter as claimed in claim 1 wherein said first and second arms are formed of a resilient plastic material.

5. A suture cutter as claimed in claim 1 wherein said first and second arms are formed of metal.

6. A suture cutter as claimed in claim 1 further comprising means connected to said first and second arms for laterally stabilizing said first and second arms.

7. A suture cutter as claimed in claim 1 wherein said first and second arms have triangular major surfaces, with said first and second arms being coupled at bases of said triangular major surfaces, and said free ends being at apexes of said triangular major surfaces.

8. A suture cutter as claimed in claim 1 wherein said first arm is resiliently coupled to said second arm.

9. A method for cutting sutures in a skin surface, comprising:

providing a handle assembly having a first arm and a second arm substantially longitudinally coextensive with and coupled at one end to the first arm, the second arm having a free end spaced away from an opposed free end of the first arm;

providing cutting means on said free end of said first arm, including a blade having a suture side-cutting edge and a skin-surface-side noncutting edge oriented at a nonzero angle with respect to the length of said first arm;

providing an anvil on said free end of said second arm;

inserting the blade between each suture and said skin surface with said skin-surface-side noncutting edge lying generally parallel to said skin surface and said first arm assuming said nonzero angle; and providing relative displacement of said anvil and said cutting edge toward one another to cut the suture.

10. A method according to claim 9 including the step of providing a straight blade edge.

11. A method according to claim 10 including the steps of forming the straight blade edge to meet with the suture side cutting edge at a leading point, and relatively displacing the anvil and said cutting edge to engage the leading point against said anvil first and before any remaining portions of the blade edge engage said anvil.

12. A suture cutter according to claim 1 wherein said skin-surface-side non-cutting edge extends linearly to meet with said straight suture side cutting edge at said leading point.

* * * * *